(12) United States Patent
Meza et al.

(10) Patent No.: US 8,927,744 B2
(45) Date of Patent: Jan. 6, 2015

(54) PROCESS AND SYSTEM FOR PRODUCING AN OXIRANE

(71) Applicants: Cesar E. Meza, Pearland, TX (US); Philip J. Carlberg, Lake Jackson, TX (US); Hannah L. Crampton, Lake Jackson, TX (US)

(72) Inventors: Cesar E. Meza, Pearland, TX (US); Philip J. Carlberg, Lake Jackson, TX (US); Hannah L. Crampton, Lake Jackson, TX (US)

(73) Assignee: Dow Global Technologies LLC, Midland, MI (US)

( * ) Notice: Subject to any disclaimer, the term of this patent is extended or adjusted under 35 U.S.C. 154(b) by 0 days.

(21) Appl. No.: 14/355,865

(22) PCT Filed: Nov. 2, 2012

(86) PCT No.: PCT/US2012/063303
§ 371 (c)(1),
(2) Date: May 2, 2014

(87) PCT Pub. No.: WO2013/067339
PCT Pub. Date: May 10, 2013

(65) Prior Publication Data
US 2014/0309441 A1    Oct. 16, 2014

Related U.S. Application Data

(60) Provisional application No. 61/555,931, filed on Nov. 4, 2011.

(51) Int. Cl.
*C07D 301/12* (2006.01)

(52) U.S. Cl.
CPC .................................... *C07D 301/12* (2013.01)

USPC ........................................................ 549/529

(58) Field of Classification Search
USPC ........................................................ 549/529
See application file for complete search history.

(56) References Cited

U.S. PATENT DOCUMENTS

| | | |
|---|---|---|
| 5,760,253 A | 6/1998 | Danner et al. |
| 6,603,027 B1 | 8/2003 | Catinat et al. |
| 6,608,219 B2 | 8/2003 | Haas et al. |
| 2003/0191327 A1 | 10/2003 | Postma et al. |
| 2009/0131693 A1 | 5/2009 | Busch et al. |
| 2011/0028745 A1 | 2/2011 | Ploemen et al. |

FOREIGN PATENT DOCUMENTS

| | | |
|---|---|---|
| EP | 1247805 | 10/2002 |
| EP | 1247806 | 10/2002 |
| WO | 03016296 | 2/2003 |
| WO | 2008087657 | 7/2008 |
| WO | 2009063487 | 5/2009 |
| WO | 2011017401 | 2/2011 |

OTHER PUBLICATIONS

International Search Report and Written Opinion for related PCT Application PCT/US2012/063303, mailed Feb. 8, 2013 (11 pgs).
Wang, Li, et al., Journal of Chemical Technology and Biotechnology (2007), 82(4), 414-420 CODEN: JCTBED; ISSN 0268-2575.

*Primary Examiner* — Kristin Vajda
(74) *Attorney, Agent, or Firm* — Brooks, Cameron & Huebsch, PLLC

(57) ABSTRACT

Embodiments of the present disclosure provide processes and systems for the epoxidation of an olefin using a fixed bed reactor. The fixed bed reactor is maintained at a temperature from 0 to 40 degrees Celsius. The processes and systems regulate a superficial liquid velocity of a non-homogeneous reaction mixture and recycled portion of effluent of the fixed bed reactor.

15 Claims, 1 Drawing Sheet

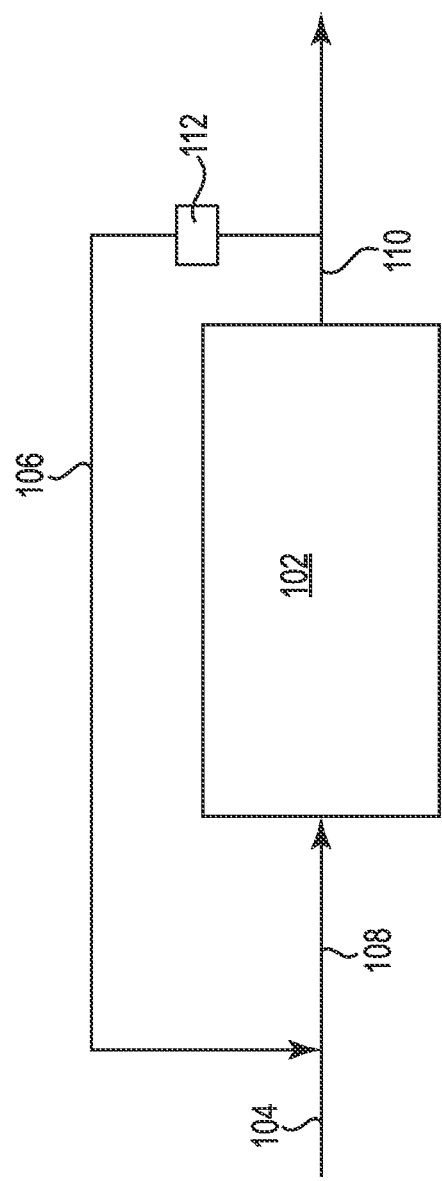

US 8,927,744 B2

PROCESS AND SYSTEM FOR PRODUCING AN OXIRANE

This application is a National Stage Application under 35 U.S.C. §371 of International Application Number PCT/US2012/063303, filed Nov. 2, 2012 and published as WO 2013/067339 on May 10, 2013, which claims the benefit to U.S. Provisional Application 61/555,931, filed Nov. 4, 2011, the entire contents of which are incorporated herein by reference in its entirety.

CROSS-REFERENCE TO RELATED APPLICATIONS

This application claims the benefit under 35 U.S.C. §119(e) of U.S. Provisional Patent Application No. 61/555,931, filed Nov. 4, 2011, which is incorporated herein by reference in its entirety.

FIELD OF DISCLOSURE

Embodiments of the present disclosure are directed to a process and a system for producing an oxirane.

BACKGROUND

Oxiranes are valuable chemicals and are useful in a variety of end use applications. Epichlorohydrin, for example, is an oxirane and a valuable chemical commodity used extensively to make epoxy resins on a commercial scale. Currently, a "chlorohydrin" process is employed for manufacturing epichlorohydrin. The process begins with the chlorohydrination of allyl chloride by reaction with an aqueous dispersion of chlorine in water. This process forms an isomeric mixture of 1,2- and 1,3-dichlorohydrin, which is subjected to dehydrochlorination in caustic solution to yield epichlorohydrin. The chlorohydrin process is used to make over 95% of epichlorohydrin produced globally, but this known process suffers from the disadvantages of producing high levels of chlorinated organic compounds and salt in waste streams, and of producing large amounts of waste water.

There are several known processes in the art that use peroxide, such as hydrogen peroxide ($H_2O_2$), to produce an oxirane, including epichlorohydrin. Such processes are described in: Clerici et al., "Epoxidation of Lower Olefins with Hydrogen Peroxide and Titanium Silicalite," Journal of Catalysis, 1993, 140, 71-83; U.S. Pat. No. 7,323,578; EP Patent Application Publication No. 1993/0549013 A1; Pandey et al., "Eco-friendly Synthesis of Epichlorohydrin Catalyzed by Titanium Silicalite (TS-1) Molecular Sieve and Hydrogen Peroxide," Catalysis Communications, 2007, 8, 379-382; Chinese Patent Application No. CN 200710039080.1; Zhang et al., "Effects of Organic Solvent Addition on the Epoxidation of Propene Catalyzed by TS-1," Reaction Kinetics and Catalysis Letters, 2007, 92(1), 49-54; Li, et al., "Epoxidation of Allyl Chloride to Epichlorohydrin by a Reversible Supported Catalyst with $H_2O_2$ Under Solvent-Free Conditions," Organic Process Research & Development, 2006, 10, 876-880; Patent application PCTUS/08/080, titled "Process for epoxidizing olefins with hydrogen peroxide using supported oxo-diperoxo tungstate catalyst complex"; and U.S. Pat. No. 6,288,248 B1.

For epoxidizing some olefins, such as allyl chloride, using a peroxide reaction catalyzed by a titanium silicalite, it is well known that methanol is a necessary component of the peroxide reaction to obtain high activity and/or selectivity. Generally, methanol must be used in large excesses in the known processes. This results in the formation of byproducts from the reaction of methanol and water, which is solubilized in the organic phase by methanol, with an oxirane. It is estimated that the use of these large quantities of methanol would result in the construction of large towers and the consumption of a large amount of energy for the purification of the oxirane product if produced on a commercial scale. Additionally, a titanium silicalite-1 (TS-1) catalyst used under these conditions would deactivate in a matter of hours; and subsequently, would have to be fully regenerated by calcination. Furthermore, the high concentration of methanol promotes the formation of by-products through the reaction of the oxirane product with methanol.

Epoxidation systems generally require higher temperatures in addition to increased methanol concentrations. Higher temperatures typically decrease selectivity and result in lower yield of the desired oxirane. That is, increased temperatures can result in increased hydrolysis and/or solvolysis of the epichlorohydrin to byproducts such as, for example, monochlorohydrin.

Some of the problems of the known processes described above may be summarized as follows:

(1) High levels of methanol must be separated from the oxirane product and recycled which creates a high energy use and associated high costs for the process and can lead to high levels of by-products.

(2) High reaction temperatures can cause hydrolysis and/or solvolysis of the oxirane and form undesired byproducts, thereby decreasing the selectivity of the desired oxirane.

It is desired to provide a system and a process for preparing an oxirane product that can be operated at reaction conditions that do not have the problems of the above described processes; that still maintains a high catalyst activity; that increases the selectivity of the reaction; and that extends the lifetime of the catalyst without the need for any additional components which would have to be removed in a subsequent downstream process.

SUMMARY

The present disclosure includes a process and a system for producing an oxirane. The process includes: providing a non-homogeneous reaction mixture of an olefin, a peroxide compound, and a solvent mixture with an alcohol and a non-reactive co-solvent to a feed stream of a fixed bed reactor; recycling at least a portion of an effluent from the fixed bed reactor to the feed stream, where the effluent contains at least some of the reaction mixture and an oxirane; providing the feed stream to the fixed bed reactor maintained at a temperature of 0 to 40 degrees Celsius; regulating a superficial liquid velocity of the reaction mixture and the portion of the effluent recycled to the feed stream through the fixed bed reactor from 50 to 350 meters per hour; and reacting the reaction mixture and the portion of the effluent recycled to the feed stream with a catalyst within the fixed bed reactor to form the oxirane.

The system of the present disclosure includes: a fixed bed reactor maintained at a temperature from 0 to 40 degrees Celsius and having a catalyst; a non-homogeneous feed stream in fluid communication with the fixed bed reactor, the feed stream including a reaction mixture of an olefin, a peroxide compound, and a solvent mixture with an alcohol and a non-reactive co-solvent; an effluent recycle stream in fluid communication with the feed stream, where the effluent recycle stream returns at least a portion of an effluent from the fixed bed reactor to the feed stream, where the portion of the effluent returned to the feed stream contains at least some of the reaction mixture and an oxirane produced from a reaction of the reaction mixture with the catalyst; and a number of pumps that provide the reaction mixture and the portion of the effluent from the fixed bed reactor recycled to the feed stream with a superficial liquid velocity through the fixed bed reactor of 50 to 350 meters per hour.

The olefin can include allyl chloride, the peroxide compound can include hydrogen peroxide solution, the alcohol can include methanol, the non-reactive co-solvent can include o-dichlorobenzene, and the oxirane can include epichlorohydrin. The catalyst can include titanium silicalite. The catalyst can be in the form of a particle having a Sauter diameter of 1.6 to 2.5 millimeters.

A volumetric flow ratio of the portion of the effluent recycled to the reaction mixture to form the feed stream can be 40 to 535. The process can include regulating the superficial liquid velocity including regulating the superficial liquid velocity of the reaction mixture and the recycled effluent through the fixed bed reactor such that the catalyst is not degraded. The process and system can include a fixed bed reactor that has a weight ratio of a liquid content to catalyst of 0.4 to 8.0, based on the reactor volume after being packed with catalyst and/or inert filler, as discussed herein.

The catalyst within the fixed bed reactor can have a column height and the volumetric flow rate of the reaction mixture can be varied such that a liquid hourly space velocity of the reaction mixture and the recycled effluent through the fixed bed reactor is 0.4 to 15 inverse hours.

The process can include providing the effluent to a number of additional fixed bed reactors in series with the fixed bed reactor.

The above summary of the present disclosure is not intended to describe each disclosed embodiment or every implementation of the present disclosure. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

BRIEF DESCRIPTION OF THE DRAWINGS

The following drawings illustrate non-limiting embodiments of the present disclosure, wherein:

FIG. 1 illustrates an embodiment of a system for producing an oxirane according to the present disclosure.

DEFINITIONS

"Oxirane" refers to a compound in which an oxygen atom is directly attached to two adjacent carbon atoms of a carbon chain or ring system. Epichlorohydrin, which is formed from an epoxidation reaction of allyl chloride, is an example of an oxirane.

"Supported solid" refers to an insoluble matrix (or support structure) formed from an organic polymer or inorganic material such as silicas or other minerals, for example, where the insoluble matrix includes active sites, such as functional groups, for the exchange of ions.

"Slurry" refers to a suspension of a solid (e.g., solid phase) in a liquid (e.g., liquid aqueous phase).

"Organic stream" refers to a mixture of at least an olefin, such as allyl chloride, and iron ions.

As used herein, "° C." is an abbreviation for degrees Celsius.

The term "and/or" means one, one or more, or all of the listed elements.

Unless otherwise indicated, all numbers expressing quantities of components, weight parts, temperatures, percentages, and so forth used in the specification and claims can be understood as being modified by the term "about."

As used herein, "a" "an" "the" "at least one" and "one or more" are used interchangeably. The terms "includes" and "comprises" and variations thereof do not have a limiting meaning where these terms appear in the description and claims. Thus, for example, a solvent mixture with an alcohol and a non-reactive co-solvent, a solid phase and reaction products of the reaction mixture can be interpreted to mean that the solvent mixture includes one or more alcohol(s), one or more non-reactive co-solvent(s), one or more solid phase(s) and one or more reaction products of the reaction mixture.

Also herein, the recitations of numerical ranges by endpoints include all numbers subsumed within that range (e.g. 1 to 5 includes 1, 1.5, 2, 2.75, 3, 3.8, 4, 5, etc.).

"Peroxide solution" refers to any solution including molecules containing one or more peroxide (—O—O—) functionalities, including organic or inorganic peroxides, peroxide adducts, or peracids.

"Iron ions" refers to the ions of iron including, but not limited to, $Fe^{3+}$, $Fe^{2+}$, $Fe^{1+}$ and combinations of $Fe^{3+}$, $Fe^{2+}$, $Fe^{1+}$ with other counterions such as $Cl^-$, e.g., $[FeCl_2]^+$.

"Piping" or "tubing" refers to a system of pipes/tubes used to convey fluids (e.g., a liquid) from one location to another location. Such piping/tubing can also include in-line components, such as fittings and valves that are used to couple the system of pipes/tubes.

"Sauter diameter" refers to the diameter of a sphere having the same volume to surface-area ratio as the particle of interest. That is, for the diameter of a particle $(D_p)$: $D_p = 6 \ast V_p/S_p$, where $V_p$ is volume of the particle and $S_p$ is the surface area of the particle. For a sphere it is known that volume $(V) = (4/3) \ast \pi r^3$ and surface-area $(S) = 4 \ast \pi r^2$. Therefore, $D_p = 6 \ast r/3 = 2r$, which is the same as the standard diameter for a sphere.

"Non-homogeneous mixture" refers to a mixture that is non-uniform. That is, a non-homogeneous mixture can have multiple phases and/or multiple insoluble compounds.

"Superficial velocity" refers to the volumetric flow rate of the fluid traveling through the pipe/reactor divided by the cross-sectional area of the pipe/reactor (without packing).

"Liquid hourly space velocity" refers to the total volumetric feed flow rate independent of recycle flow rate (total reaction mixture) of liquid components divided by volume of catalyst loaded in the reactor vessel.

"Epichlorohydrin selectivity" (Epi Sel.) refers to the total moles of epichlorohydrin (Epi) produced divided by the total moles of Epi and the two main by-products, 1-chloro-2,3 propane diol (MCH) and 1-chloro-3-methoxypropanol (CMP):

$$EpiSel. = \frac{\text{moles of } Epi \text{ produced}}{\text{moles of } (Epi + MCH + CMP)_{produced}}$$

DETAILED DESCRIPTION

Embodiments of the present disclosure provide a process for producing an oxirane, such as, for example, epichlorohydrin. A non-homogeneous reaction mixture including an olefin, a peroxide compound, and a solvent mixture with an alcohol and a non-reactive co-solvent is provided to a feed stream of a fixed bed reactor. A portion of an effluent from the fixed bed reactor is recycled to the feed stream. The feed stream is provided to the fixed bed reactor at a temperature of 0 to 40 degrees Celsius. The non-homogeneous reaction mixture and portion of the effluent recycled to the feed stream are regulated so that a superficial liquid velocity through the fixed bed reaction is 50 to 350 meters per hour. The non-homogenous reaction mixture and portion of the effluent recycled are reacted in the fixed bed reactor to form the oxirane.

The problems of the prior processes may be solved by the process of the present disclosure which provides an epoxidation process for producing an oxirane product, such as epichlorohydrin, for example from allyl chloride and hydrogen peroxide, catalyzed by, for example, titanium silicalite-1 (TS-1), in a mixed solvent system. Unlike prior art systems and processes, however, the system and process of the present disclosure can produce the oxirane using lower amounts of total organic solvent and much lower amounts of methanol than prior processes.

The present disclosure provides such an advantage because it provides a process and a system that utilizes a non-homogeneous reaction mixture. A non-homogenous reaction mixture includes a mixture that contains two immiscible liquid phases: a liquid organic phase and a liquid aqueous phase. The non-homogeneous reaction mixture can also include a solid phase, for example a catalyst. The oxirane preferentially partitions (e.g., sequesters) into the liquid organic phase, thereby reducing its contact with water and methanol of the liquid aqueous phase. This helps to reduce byproducts resulting from hydrolysis and/or solvolysis of the oxirane. This both increases the selectivity of the reaction and extends the lifetime of the catalyst without the need for any additional components in the reaction mixture, which would have to be removed in the downstream process. The non-homogeneous nature of the reaction mixture also facilitates the subsequent recovery of the oxirane, such as epichlorohydrin, by allowing a separation of the liquid aqueous phase and the liquid organic phase by, for example, decantation, prior to recovery of recyclable and useful product components from each stream.

In addition, the present disclosure provides advantages over prior processes because the methanol concentrations used in the present disclosure are lower than those presented in previously known processes. This helps to decrease losses of oxirane to solvolysis by methanol, thereby increasing the selectivity and helping to maximize peroxide use.

Embodiments of the present disclosure include a process and a system that provide a non-homogeneous reaction mixture to a feed stream of a fixed bed reactor. The non-homogeneous reaction mixture includes an olefin, a peroxide compound, a solvent mixture with an alcohol and a non-reactive co-solvent.

As discussed more fully herein, the non-homogeneous reaction mixture can include (a) at least one olefin wherein the olefin is selected from one of (i) an aliphatic olefin or substituted aliphatic olefin, (ii) a cycloaliphatic olefin, (iii) an aromatic olefin, (iv) a cycloaromatic olefin, and (v) mixtures thereof; with (b) at least one peroxide compound, in the presence of (c) the solid phase (e.g., at least one catalyst) and (d) in the presence of a solvent mixture; wherein the solvent mixture comprises at least (i) at least one alcohol or a combination of alcohols and (ii) at least one non-reactive co-solvent.

The olefin useful in the process and system of the present disclosure may comprise acyclic or cyclic aliphatic or aromatic olefins, including those which may contain multiple double bonds. Examples of the olefin include, but are not limited to, chloride-butadiene and other linear dialkenes, cyclohexene and other cyclic alkenes and dialkenes, substituted alkenes, such as halogenated alkenes, styrene, divinylbenzene, dicyclopentadiene, other aromatic alkenes and mixtures thereof. Moreover, butenes, pentenes, hexenes, octenes, heptenes, 1-tridecene, mesityl oxide, isoprene, cyclo-octane, cyclohexene or bicyclic compounds such as norbornenes or pinenes may also be used. Other olefins useful in the process of the present disclosure may also include, for example, but are not limited to, other linear alkenes of formula $C_nH_{2n}$; butadiene and other linear dialkenes of formula $C_nH_{2n-2}$; cyclohexene and other cyclic alkenes and dialkenes; substituted alkenes, such as halogenated alkenes; styrene; divinylbenzene; dicyclopentadiene; and other aromatic alkenes and mixtures thereof. The system of the present disclosure may also be extended to the oxidation of aliphatic and aromatic alkanes and alcohols, such as, but not limited to, hexane, benzene, hexanol and phenol.

The concentration of the at least one olefin is from 10 percent by weight (wt %) to 90 wt %, preferably from 20 wt % to 80 wt %, more preferably from 25 wt % to 70 wt %, and most preferably from 25 wt % to 50 wt %, based on the weight of the components of the non-homogeneous reaction mixture provided to the feed stream of the fixed bed reaction vessel. In a preferred embodiment of the present disclosure the olefin can include allyl chloride.

As used herein, "peroxide compound" refers to a compound containing one or more peroxide (—O—O—) functionalities, including organic or inorganic peroxides, peroxide adducts, peracids or combinations thereof. These can include, for example, but are not limited to, hydrogen peroxide, urea-hydrogen peroxide adduct, peracetic acid, and mixtures thereof.

The concentration of the peroxide compound may generally be from 1 wt % to 35 wt %, preferably from 1 wt % to 20 wt %, more preferably from 1 wt % to 15 wt %, and most preferably from 1 wt % to 10 wt %, based on the weight of the components of the non-homogeneous reaction mixture provided to the feed stream of the fixed bed reaction vessel.

A variety of peroxide compounds can be used in the non-homogeneous reaction mixture of the present disclosure. Examples of the peroxide compounds useful in the present disclosure may include, but are not limited to, organic and/or inorganic hydroperoxides, such as hydrogen peroxide, tert-butyl hydroperoxide, ethylbenzene hydroperoxide, acetyl peroxide, benzoyl peroxide, methyl ethyl ketone peroxide, cumene peroxide and combinations thereof. In the present disclosure, preference is given to using hydrogen peroxide as the peroxide compound. The present disclosure as described herein, therefore, also provides a process for using hydrogen peroxide as the peroxide compound. Here, preference is given to using an aqueous hydrogen peroxide.

The non-homogeneous reaction mixture can include a solvent mixture; wherein the solvent mixture comprises at least (i) at least one alcohol or a combination of two or more alcohols, and (ii) at least one non-reactive co-solvent other than the solvent component (i); wherein the co-solvent has a different boiling point than the olefin and the oxirane. The solvent mixture is selected to include at least one solvent having properties such that the oxirane partitions into the at least one solvent present in the solvent mixture during the reaction. The at least one solvent is said to have a high affinity for the oxirane.

"Partitions" herein refers to the tendency of the oxirane product to be more soluble in the solvent mixture phase than in the other phase or phases present in the reaction mixture. It is quantified by the ratio of the oxirane product concentration in the solvent mixture phase to the total amount of oxirane product in the reaction mixture. Generally, the solvent is selected so that 90 wt % or more of the total weight of the oxirane product in the reaction mixture resides in the solvent mixture phase. Preferably, more than 99 wt % of the total weight of the oxirane product resides in the solvent mixture phase. Most preferably, 99.9 wt % or more of the total weight of the oxirane product resides in the solvent mixture phase.

For the embodiments of the present disclosure, an alcohol or a mixture of two or more alcohols can be used as the first solvent component of the solvent mixture. The alcohols may include, for example, lower alcohols such as alcohols having less than 6 carbon atoms, for example methanol, ethanol, propanols (e.g. isopropanol), butanols (e.g. tert-butanol) and pentanols and a combination of two or more of these alcohols; halogenated alcohols; and mixtures thereof. Preference is given to using an alcohol with one to four carbon atoms (or mixtures thereof), and more specifically to using methanol as the alcohol for the first solvent component. In particular, methanol not only acts as a solvent, but also acts as an activator for the catalyst.

The concentration of the alcohol(s) is generally from 3 wt % to 40 wt %, preferably from 3 wt % to 20 wt %, more preferably from 3 wt % to 10 wt %, and most preferably from 3 wt % to 7 wt %, based on the weight of the components of the non-homogeneous reaction mixture provided to the feed stream of the fixed bed reaction vessel.

As discussed herein, the non-homogeneous reaction mixture can include a non-reacting co-solvent. The non-reacting co-solvent can include a compound which is inert to the epoxidation reaction. For example, the non-reacting co-solvent does not take part in the reaction under the reaction conditions, does not react appreciably with the peroxide compound or the oxirane under reaction conditions, is minimally soluble in water, and has a boiling point substantially different than the oxirane to be produced from the epoxidation reaction.

Examples of the non-reacting co-solvent(s) can include, but are not limited to, aliphatic, cycloaliphatic, and aromatic hydrocarbons. Additionally, the non-reacting co-solvent(s) can include, but is not limited to, linear and cyclic alkanes of three to eighteen carbon atoms, halogenated hydrocarbons, deactivated aromatics, and solvents containing nitriles, e.g., acetonitrile; or mixtures thereof. For example, the non-reacting co-solvent may include, but is not limited to, carbon tetrachloride, propyl chloride, chloroform, dichloromethane, dichloroethane, hexane, octane, decalin, perfluorodecalin, mono- or poly-chlorinated benzenes, mono- or poly-brominated benzenes, acetophenone, benzonitrile, acetonitrile, trichlorotrifluoroethane, trichloroethanol, trifluoroethanol, tricresyl phosphate, or mixtures of two or more of the above-mentioned compounds. For one or more embodiments, the non-reacting co-solvent is 1,2-dichlorobenzene.

In a particularly advantageous embodiment of the present disclosure, the non-reacting co-solvent may be selected from those which have solubility parameters similar to the olefin to be epoxidized, as estimated using Hansen parameters and a Teas plot. Preferred non-reacting co-solvents are chosen from, but are not limited to, those with hydrogen bonding force from 0.0 to 0.3, dispersion force from 0.4 to 1.0, and polar force from 0.0 to about 0.5. These solvents will have a high affinity for the olefin to be epoxidized, such as epichlorohydrin, and a low affinity for water, resulting in increased sequestration of the olefin to be epoxidized, such as epichlorohydrin, in the liquid organic phase. The addition of the non-reacting co-solvent(s) can increase the catalyst lifetime by reducing the plugging of the catalyst pores, as discussed herein.

The concentration of the non-reacting co-solvent is generally from 5 wt % to 70 wt %, preferably from 10 wt % to 65 wt %, more preferably from 25 wt % to 55 wt %, and most preferably from 30 wt % to 55 wt %, based on the weight of the components of the non-homogeneous reaction mixture provided to the feed stream of the fixed bed reaction vessel.

Other optional components, that may be useful in the present disclosure, are components normally used in epoxidation reactions known to those skilled in the art. For example, the optional components may comprise compounds that can be added to the composition to enhance the reaction rate, the selectivity of the reaction, and/or the catalyst lifetime. The preferred optional components and their relative concentrations useful in the composition of the present disclosure can be determined by the skilled artisan.

As an illustration of one embodiment, the present disclosure may be directed to a specific mixture of a small amount (e.g., 3 wt %-7 wt %) of methanol along with a non-reacting co-solvent, with an excess of an olefin compound, such as allyl chloride, such that the olefin is from 30 wt % to 50 wt %, based on the weight of the components of the non-homogeneous reaction mixture provided to the feed stream of the fixed bed reaction vessel, making the olefin such as allyl chloride the main solvent. The resulting reaction mixture consists of at least two liquid phases, the solid catalyst, and a vapor phase which is in contact with the other phases or components present in the reaction mixture, which increases the selectivity of the reaction without the need for other additives.

The non-homogeneous reaction mixture described herein is provided to a feed stream of the fixed bed reactor according to embodiments of the present disclosure. The reaction for the preparation of an oxirane can be carried out in the reaction vessel herein by any continuous method. In one embodiment, the process herein may be carried out in more than one reaction vessel.

At least a portion of the effluent from the fixed bed reactor is recycled to the feed stream of the fixed bed reactor. The portion of the effluent recycled to the feed stream includes at least some of the reaction mixture and the oxirane, as described herein. Per visual inspection, for example, sufficient mixing can be determined by the absence of stratification and/or absence of bubbles larger than 1 mm, as calculated from the recycle stream flow rate.

Increasing the velocity of the recycle effluent stream to the feed of the reaction vessel is important for maintaining the same reactant ratio and more uniform distribution of the number of components of the reaction mixture and recycle effluent into the bed of the reaction vessel. The volumetric flow rate of the effluent recycle stream can be sufficiently high enough to provide adequate mixing with the feed stream. Increasing the volumetric flow ratio of recycled effluent to reaction mixture (recycled effluent/reaction mixture) can improve selectivity. In one embodiment the recycled effluent to reaction mixture volumetric flow ratio (recycled effluent/reaction mixture) is preferably from 40 up to 535, more preferably from 120 up to 350, and most preferably from 250 up to 350.

The temperature and pressure of the fixed bed reactor can be controlled during the preparation of the oxirane from an olefin and a peroxide compound. The temperature of the fixed bed reactor is preferably from 0 degrees Celsius to 40 degrees Celsius, more preferably from 5 degrees Celsius to 35 degrees Celsius, and most preferably from 10 degrees to 25 degrees Celsius.

The temperature of the reaction vessel can be controlled by any known means. The temperature can be controlled according to the composition of the non-homogeneous reaction mixture and effluent recycle stream. In an embodiment the fixed bed reactor includes a cooling jacket to control the temperature of the vessel. In an additional embodiment, an external heat exchanger can provide sufficient cooling to maintain the reaction vessel within a preferable temperature range.

Processes and systems according to the present disclosure regulate a superficial liquid velocity of the non-homogeneous reaction mixture and the recycled effluent through the fixed bed reactor. In one particular embodiment the superficial liquid velocity is varied such that the catalyst is not degraded. The superficial liquid velocity of the non-homogeneous reaction mixture and the recycled effluent through the fixed bed reactor is preferably from 50 to 350 meters/hour, more preferably from 100 to 300 meters/hour, and most preferably from 200 to 300 meters/hour.

In the processes and system of the present disclosure, a liquid hourly space velocity (LHSV) of the non-homogeneous reaction mixture and the recycled effluent through the fixed bed reactor can be controlled. Liquid hourly space velocity of the contents in the fixed bed reactor is preferably from 0.4 to 15 $hr^{-1}$, more preferably from 0.4 to 10 $hr^{-1}$, and most preferably from 0.4 to 5 $hr^{-1}$.

The non-homogeneous reaction mixture and portion of the effluent recycled to the feed stream are reacted with a catalyst within the fixed bed reactor to form the oxirane. As used herein, a "catalyst" can be a heterogeneous catalyst appropriate for the epoxidation of an olefin. These may include, but are not limited to, heterogenized forms of soluble metal catalysts such as ligand-bound rhenium, tungsten, and manganese, as well as solid silicalite catalysts that preferably contain titanium. These solid catalysts may have the crystal structure of ZSM-5, MCM-22, MCM-41, beta-zeolites, or amorphous titanium on silica.

Preference is given to a heterogeneous catalyst and particularly to a heterogeneous catalyst which comprises a porous oxide material such as zeolite. In general, the catalyst may include, but is not limited to, titanium-, vanadium-, chromium-, niobium- or zirconium-containing zeolite as the porous oxide material.

Specific examples of suitable zeolites are titanium-, vanadium-, chromium-, niobium- and zirconium-containing zeolites having a pentasil zeolite structure, in particular the types assigned X-ray-crystallographically to the BEA, MOR, TON, MTW, FER, MFI, MEL, CHA, ERI, RHO, GIS, BOG, NON, EMT, HEU, KFI, FAU, DDR, MTT, RUT, RTH, LTL, MAZ, GME, NES, OFF, SGT, EUO, MFS, MWW or mixed MFI/MEL structures and also ITQ-4. It is also possible to use titanium-containing zeolites having the UTD-1, CIT-1 or CIT-5 structure in the process of the present disclosure. Further titanium-containing zeolites which might be mentioned are those having the ZSM-48 or ZSM-12 structure. Particular preference is given to using Ti zeolites having an MFI, MEL or mixed MFI/MEL structure in the process of the present disclosure. Further preference is given, specifically, to the Ti-containing zeolite catalysts which are generally designated as "TS-1", "TS-2" and "TS-3", and also Ti zeolites having a skeletal structure isomorphous with MWW-zeolite.

Particular preference is given to using a heterogeneous catalyst comprising the titanium-containing silicalite TS-1 in the process of the present disclosure.

It is possible to use the porous oxidic material itself as catalyst in the process of the present disclosure. However, it is of course also possible to use a shaped body comprising the porous oxidic material as catalyst. The shaped body from the porous oxidic material may be produced using known methods.

The concentration of the catalyst is generally from 0.1 wt % to 80 wt %, preferably from 0.1 wt % to 50 wt %, more preferably from 1 wt % to 40 wt %, and most preferably from 5 wt % to 30 wt %, based on the on total contents of reactor and the total contents of the recycle stream.

As discussed herein, the solid phase catalyst can have an affinity for the liquid aqueous phase. As used herein, "affinity", or "chemical affinity", refers to an attraction or force by which dissimilar chemical species, e.g., the solid phase and liquid aqueous phase, have a tendency to associate with one another. The affinity of the solid phase catalyst for the liquid aqueous phase is due to Van der Waals forces, hydrogen bonding, ionic interactions, and combinations thereof.

The catalyst can include a polar group, a charged group, or a combination thereof to provide the affinity of the solid phase for the liquid aqueous phase. The polar group can include, but is not limited to —OH, —$NR_2$, phosphorous, sulfur, boron, and combinations thereof. The charged group can include, but is not limited to $O^-$, $N^-$, metal ions, and combinations thereof.

The catalyst can be chosen based on the Sauter diameter of the catalyst. In a preferred embodiment the catalyst has a Sauter diameter of 1.6 to 2.5 millimeters.

The catalyst is typically in solid form in the non-homogeneous reaction mixture, while the reaction is carried out in the presence of two immiscible liquid phases, the liquid organic phase and the liquid aqueous phase. The solid form of the catalyst can be powders or extrudates for fixed bed reaction vessels. The amounts of the individual components for the embodiment should be selected based on their physical properties such that when mixed together the liquid composition comprises the immiscible liquid organic phase and liquid aqueous phase.

A weight ratio of liquid content, including the non-homogeneous reaction mixture and recycled effluent, to catalyst weight is preferably from 0.4 to 8.0, more preferably from 1.0 to 3.0, and most preferably from 1.0 to 2.5. The weight ratio of liquid content is calculated after the reaction vessel has been packed with catalyst and/or inert filler accounting for the bed void fraction.

As described herein, the volumetric flow rate of the recycled effluent stream, volumetric flow rate of the feed stream to the fixed bed reactor, the superficial liquid velocity and LHSV of the non-homogeneous reaction mixture and portion of the effluent recycled, characteristics of the catalyst, and/or reaction vessel type can be varied so that a pressure drop across the packed bed is within a preferred range. In one or more embodiments the pressure drop across the packed bed is from 5 to 45 psig, more preferably from 5 to 25 psig, and most preferably from 5 to 15 psig.

With respect to the processes and systems of the present disclosure, a variety of suitable reactor arrangements may be useful in the present disclosure. Thus, for example, the oxirane can be prepared in a cascade of two or more reaction vessels connected to one another in series. Conceivable processes useful in the present disclosure also include for example those in which reaction vessels are arranged in parallel. Combinations of these processes and systems are also possible. In the case where two or more reaction vessels are connected in series, suitable intermediate treatments can also be provided between the reaction vessels. The reactors can be oriented in a variety of directions, so that flow is in the upward direction, downward direction, or in a horizontal direction.

In one embodiment, the process of the present disclosure produces a waste stream with little, or no significant amount of, sodium chloride (NaCl). By "no significant amount" with reference to the sodium chloride it is meant herein as generally less than about 1 wt %, preferably less than about 0.5 wt %, and most preferably less than about 0.1%, based on the weight of the total composition.

In one or more embodiments, it is preferred to remove any "dead space" within the reaction vessel. Dead space refers to space in which the contents of the feed stream and/or effluent can collect within the reaction vessel and not maintain contact with the fixed bed. Dead space is undesirable as it can lead to improper mixing of the non-homogenous mixture leading to poor reactant dispersion and consequently reduce selectivity. In one or more embodiments a section of non-reactive material fashioned to fit inside of the reactor can be placed in the reaction vessel to remove the dead space and create and jet-like feed stream into the bed. Non-reactive material can include, but is not limited to, TEFLON®. Further, a layer of non-reactive glass beads can be placed below and above the catalyst support to remove any dead space. For example, if the feed stream is fed to the top of the reaction vessel, the top layer of glass beads can aid in distributing the incoming flow better over the catalyst and minimize catalyst degradation. The bottom layer of glass beads can act as a second type of packing support.

FIG. 1 illustrates a reaction vessel 102 used in the system and process according to an embodiment of the present disclosure. Stream 104 is the non-homogeneous reaction mixture stream including the olefin, the peroxide compound, and the solvent mixture with an alcohol and a non-reactive co-solvent. The reaction mixture can include a liquid aqueous phase, and a liquid organic phase.

The effluent 110 of reaction vessel 102 includes the contents of the reaction mixture and the oxirane that results from the epoxidation reaction. The effluent can also contain a number of byproducts as discussed herein.

At least a portion of the effluent 110 is recycled 106 to the feed stream 108 to the reaction vessel 102. The feed stream 108 includes the contents of the non-homogeneous reaction mixture of 104 and the recycled portion of the effluent 106. The portion of the effluent recycled 106 is pumped via pump 112. In one or more embodiments of the present disclosure, a number of additional pumps can be placed on the reaction mixture stream 104, for example, to achieve the desired volumetric flow rates. The feed stream 108 is fed to the reaction vessel 102 so that the contents of the feed stream have a superficial liquid velocity through the reaction vessel 102 of 50 to 350 meters per hour.

Embodiments of the present disclosure can also include a system and a process for removing iron ions from the liquid organic phase of the non-homogenous reaction mixture stream 104. For example, a liquid organic stream and a liquid aqueous stream can combine to form the non-homogeneous reaction mixture stream 104. Prior to the liquid organic stream and the liquid aqueous streams combining the iron ions can be removed from the liquid organic stream.

The oxirane product prepared by the system and process of the present disclosure can be used in various applications. In particular, the oxirane, such as epichlorohydrin, produced by the system and process of the present disclosure can be used in the production of epoxy resins as described, for example, in Ullman's Encyclopedia of Industrial Chemistry, 5. ed., Vol. A9, pp. 547-562, incorporated herein by reference. Epoxy resins are high performance thermosetting resins which are used, for example, in coatings, electrical laminates, electronic encapsulants, adhesives, and composites.

As an illustration of the present disclosure, epichlorohydrin produced by the process of the system and present disclosure can also be used in the production of synthetic glycerine, elastomers, specialty water treatment chemicals, and wet strength resins for paper production and surfactants.

EXAMPLES

The following examples further illustrate the present disclosure in detail, but are not to be construed to limit the scope of the disclosure.

Epoxidation Reaction Examples

The following Examples 1-14 and Comparative Examples A-I illustrate various embodiments of the process for producing the oxirane by an epoxidation reaction.

Materials

Catalyst, titanium silicalite zeolite (TS-1), available from Süd-Chemie.
Olefin, allyl chloride (99.4% purity), obtained from The Dow Chemical Company.
Peroxide compound, hydrogen peroxide solution (30 wt %/aq to 50 wt %/aq), available from VWR.
Alcohol, Methanol, available from Sigma Aldrich.
Oxirane, epichlorohydrin, available from Sigma Aldrich.
Non-reactive co-solvent, 1,2-dichlorobenzene, available from Sigma Aldrich.
Water
Test Methods
Gas Chromatography (GC)
Gas chromatography was performed on an HP 6890 series G1530A GC with an HP 7682 series injector and FID detection. An HP-1701 14% cyanopropyl phenyl methyl column of length 60.0 m, diameter 320.00 μm, and thickness 1.00 μm was used at temperatures from 35° C. to 250° C.
Reaction Vessel
Table 1 summarizes a number of parameters for the following examples.

TABLE 1

| Conditions/Results Values after 8 hours of operation | | Exp. Values (near Steady State (2 hr Avg)) | | | |
|---|---|---|---|---|---|
| | | Run 1 | Run 2 | Run 3 | Run 4 |
| Organic Feed Composition | | | | | |
| Allyl Chloride | wt % | 50.2 | 50.6 | 44.9 | 44.8 |
| o-Dichlorobenzene | wt % | 43.1 | 42.8 | 48.6 | 48.6 |
| Methanol | wt % | 6.20 | 6.17 | 5.92 | 6.11 |
| Aqueous Feed Composition | | | | | |
| Hydrogen Peroxide | wt % | 35.0 | 35.0 | 35.0 | 35.0 |
| Water | wt % | 65.0 | 65.0 | 65.0 | 65.0 |
| Molar Feed Ratios | | | | | |
| Allyl/H2O2 | | 4.2 | 2.9 | 2.6 | 2.9 |
| Allyl/MeOH | | 3.4 | 3.4 | 3.2 | 3.1 |
| Allyl/o-DCB | | 2.2 | 2.3 | 1.8 | 1.8 |
| Organic Feed rate | mL/min | 6.75 | 5.00 | 4.98 | 10.33 |
| Aqueous Feed rate | mL/min | 0.94 | 1.04 | 1.03 | 1.93 |
| Cat. Bed Middle Temperature | ° C. | 11.0 | 40.0 | 40.0 | 40.0 |
| Catalyst Form | | Beads | Beads | Beads | Beads |
| Catalyst Charge | g | 200 | 150 | 600 | 40.1 |

TABLE 1-continued

Conditions/Results
Values after 8 hours of operation

| | | Exp. Values (near Steady State (2 hr Avg)) | | | |
|---|---|---|---|---|---|
| | | Run 1 | Run 2 | Run 3 | Run 4 |
| Catalyst Status | | Fresh | Fresh | Fresh | Fresh |
| Recycle Flow Rate | mL/min | 2100 | 1950 | 2100 | 2500 |
| LHSV | hr$^{-1}$ | 1.84 | 1.93 | 0.48 | 14.68 |
| $H_2O_2$ in the Effluent | wt % | 19.4 | 6.74 | 0.30 | 28.8 |
| Epi Productivity | lbs/hr/ft$^3$ cat | 9.9 | 18.2 | 4.26 | 25.3 |
| Epi Selectivity | % | 98.2 | 83.2 | 77.2 | 90.2 |
| Allyl Conversion | % | 29.4 | 31.6 | 46.6 | 21.5 |
| $H_2O_2$ Conversion | % | 15.0 | 75.6 | 98.9 | — |

Example 1

Run 1

This experiment covers the optimum operating condition to yield the highest selectivity for at least 8 hrs of operation, even up to 24 hours of operation. The reactor operated at a temperature of 10° C. and a Space velocity of 1.8 hr$^{-1}$, to yield an Epi selectivity of 98.2%.

Example 2

Run 2

This experiment was conducted to illustrate the effects of temperature at similar LHSV values. This run operated at a reactor temperature of 40° C. and a space velocity of 1.9 hr$^{-1}$, to yield an Epi selectivity of 83.2%. Even though there is an improvement in the other two governing parameters (e.g. productivity and a reduction in the peroxide concentration in the effluent) the selectivity drastically decreased.

Examples 3 and 4

Runs 3 and 4

These examples are comparative examples to Example 2 as means to demonstrate the effects of varying the LHSV while operating at the same reactor temperature of 40° C. Examples 2-4 cover the entire range of LHSV claimed. It shows that as the LHSV increases from (0.48 to 14.7 hr$^{-1}$) the Epi selectivity improves (not matching the 98% of the cold temperature) while the $H_2O_2$ concentration in the effluent increases (e.g. peroxide conversion decreases).

Pressure Drop

Table 2 summarizes a pressure drop realized over the catalyst bed within the reactor during process runs at the indicated reaction mixture compositions and recycle stream flow rates.

TABLE 2

| | Pressure Drop | | | | | |
|---|---|---|---|---|---|---|
| | Experimental | | | | | |
| Target Inlet Volumetric Reaction Mixture Ratio Aq:Org | Inlet Volumetric Reaction Mixture Ratio Aq:Org | Recycle Flow Rate mL/min | Top Pressure psig | Bottom Pressure psig | Pressure Drop psig |
| 1:5 | 1.03:4.98 | 2162 | 43 | 4.3 | 38.7 |
| 5:25 | 5.06:24.33 | 2633 | 72 | 31.7 | 40.3 |
| 1:5 | 0.85:5.13 | 1868 | 37.2 | 27.6 | 9.6 |
| 2:10 | 1.92:10.3 | 2530 | 44.8 | 31.2 | 13.6 |
| 1.5:7.5 | 1.51:7.86 | 2545 | 46.6 | 23.7 | 22.9 |
| 1:5 | 1.01:5.1 | 2100 | 46.7 | 9.4 | 37.3 |

What is claimed is:

1. A process, comprising:
    providing a non-homogeneous reaction mixture of an olefin, a peroxide compound, and a solvent mixture with an alcohol and a non-reactive co-solvent to a feed stream of a fixed bed reactor;
    recycling at least a portion of an effluent from the fixed bed reactor to the feed stream, where the effluent contains at least some of the reaction mixture and an oxirane;
    providing the feed stream to the fixed bed reactor maintained at a temperature of 0 to 40 degrees Celsius;
    regulating a superficial liquid velocity of the reaction mixture and the portion of the effluent recycled to the feed stream through the fixed bed reactor from 50 to 350 meters per hour; and
    reacting the reaction mixture and the portion of the effluent recycled to the feed stream with a catalyst within the fixed bed reactor to form the oxirane.

2. The process of claim 1, where the olefin is allyl chloride, the peroxide compound is hydrogen peroxide solution, the alcohol is methanol, the non-reactive co-solvent is o-dichlorobenzene, and the oxirane is epichlorohydrin.

3. The process of claim 1, where the catalyst is titanium silicalite.

4. The process of claim 1, where the catalyst is in the form of a particle having a Sauter diameter of 1.6 to 2.5 millimeters.

5. The process of claim 1, where a volumetric flow ratio of the portion of the effluent recycled to the feed stream to the reaction mixture in the feed stream is 40 to 535.

6. The process of claim 1, where regulating the superficial liquid velocity includes regulating the superficial liquid velocity of the reaction mixture and the recycled effluent through the fixed bed reactor such that the catalyst is not degraded.

7. The process of claim 1, where the catalyst within the fixed bed reactor has a column height and a volumetric flow rate of the reaction mixture such that a liquid hourly space velocity of the reaction mixture through the fixed bed reactor is 0.4 to 15 inverse hours.

8. The process of claim 1, including providing the effluent to a number of additional fixed bed reactors in series with the fixed bed reactor.

9. A process, comprising:
    providing a non-homogeneous reaction mixture of an olefin, a peroxide compound, and a solvent mixture with an alcohol and a non-reactive co-solvent to a feed stream of a fixed bed reactor;

recycling at least a portion of an effluent from the fixed bed reactor to the feed stream, where the effluent contains at least some of the reaction mixture and an oxirane; and regulating a superficial liquid velocity of the reaction mixture and the portion of the effluent recycled to the feed stream bed reactor such that a catalyst for reacting the reaction mixture and the portion of the effluent recycled to the feed stream to form the oxirane is not degraded.

10. The process of claim 9, where the olefin is allyl chloride, the peroxide compound is hydrogen peroxide solution, the alcohol is methanol, the non-reactive co-solvent is o-dichlorobenzene, and the oxirane is epichlorohydrin.

11. The process of claim 9, where the catalyst is titanium silicalite.

12. The process of claim 9, where the catalyst is in the form of a particle having a Sauter diameter of 1.6 to 2.5 millimeters.

13. The process of claim 9, where a ratio of a volumetric flow of the portion of the effluent recycled to the feed stream to a volumetric flow of the feed stream is 40 to 535.

14. The process of claim 9, where the catalyst within the one or more fixed bed reactors has a column height and a volumetric flow rate of the reaction mixture such that a liquid hourly space velocity through the one or more fixed bed reactors is in a range of 0.48 to 15 inverse hours.

15. The process of claim 9, where the one or more fixed bed reactors has a weight ratio of a liquid content to catalyst of 0.4 to 8.0.

* * * * *